(12) United States Patent
Brzychczy-Wloch et al.

(10) Patent No.: US 10,048,263 B2
(45) Date of Patent: Aug. 14, 2018

(54) **DIAGNOSTIC TEST OF *STREPTOCOCCUS AGALACTIAE* INFECTIONS**

(71) Applicants: UNIWERSYTET JAGIELLOŃSKI, Kraków (PL); INSTYTUT IMMUNOLOGII I TERAPII DÓSWIADCZALNEJ IM. LUDWIKA HIRSZFELDA PAN, Wroclaw (PL)

(72) Inventors: Monika Brzychczy-Wloch, Kraków (PL); Sabina Górska, Jaroslaw (PL); Ewa Brzozowska, Brzeg Dolny (PL); Andrzej Gamian, Wroclaw (PL); Piotr Heczko, Kraków (PL)

(73) Assignees: Uniwersytet Jagiellonski, Cracow (PL); Instytut Immunologii I Terapii Doswiadczainej Im. Ludwika Hirszfelds Pan, Wroclaw (PL)

( * ) Notice: Subject to any disclaimer, the term of this patent is extended or adjusted under 35 U.S.C. 154(b) by 0 days.

(21) Appl. No.: 14/900,620

(22) PCT Filed: Mar. 28, 2014

(86) PCT No.: PCT/PL2014/050018
§ 371 (c)(1),
(2) Date: Dec. 22, 2015

(87) PCT Pub. No.: WO2014/209142
PCT Pub. Date: Dec. 31, 2014

(65) Prior Publication Data
US 2016/0377613 A1     Dec. 29, 2016

(30) Foreign Application Priority Data

Jun. 28, 2013 (PL) .......................... 404498

(51) Int. Cl.
*G01N 33/569* (2006.01)
*C07K 14/315* (2006.01)

(52) U.S. Cl.
CPC ..... *G01N 33/56944* (2013.01); *C07K 14/315* (2013.01)

(58) Field of Classification Search
None
See application file for complete search history.

(56) References Cited

U.S. PATENT DOCUMENTS 6,245,335 B1     6/2001   Masure et al.
2003/0232976 A1*  12/2003  Hamel .............. C07K 14/3156
                                                          536/23.1

FOREIGN PATENT DOCUMENTS

WO     WO-0234771 A2 *   5/2002   ........... C07K 14/315

OTHER PUBLICATIONS

International Search Report and Written Opinion issued in corresponding International Patent Application No. PCT/PL2014/050018 dated Jul. 31, 2014 (18 pages).
Brzychczy-Wloch et al., "Identification of high immunoreactive proteins from *Streptococcus agalactiae* isolates recognized by human serum antibodies," FEMS Microbiology Letters, 2013, vol. 349, pp. 61-70.
Das et al., "Rapid diagnosis of vaginal carriage of group B beta haemolytic streptococcus by an enrichment cum antigen detection test," Indian Journal of Medical Research, vol. 117, No. 1, 2003, pp. 247-252.
Fluegge et al., "Identification and immunoreactivity of proteins released from *Streptococcus agalactiae*," European Journal of Clinical Microbiology & Infectious Diseases, vol. 23, No. 11, 2004, pp. 818-824.
Database, UniProt, "Trigger factor; EC=5.2.1.8, PPlase," XP002727359, UniProt: Q3DD87, Nov. 22, 2005, (1 page).
Database, UniProt, "Aldehyde dehydrogenase family protein," XP002727360, UniProt: F8Y0Y3, Oct. 19, 2011, (1 page).
Database, UniProt, "Elongation factor Tu (EF-Tu)," XP002727361, UniProt: Q8E0H1, Mar. 1, 2003, (1 page).

\* cited by examiner

*Primary Examiner* — S. Devi
(74) *Attorney, Agent, or Firm* — Kilyk & Bowersox, P.L.L.C.

(57) ABSTRACT

The method of the invention allows confirmation of infections caused by *Streptococcus agalactiae* bacterial species. The method employs a specific reaction of immunoreactive proteins obtained from clinical isolates of *Streptococcus agalactiae* with antibodies present in the serum of patients.

4 Claims, 2 Drawing Sheets

Seq. Id. No. 1

MSTSFENKAT NRGIITFTIS QDEIKPALDQ AFNKVKKDLN VPGFRKGHMP
RTVFNQKFGE EALYENALNL VLPKAYEAAV AELGLDVVAQ PKIDVVSMEK
GQDWKLTAEV VTKPEVKLGD YKDLSVEVDA SKEVSDEEVD AKVERERNNL
AELTVKDGEA AQGDTVVIDF VGSVDGVEFD GGKGDNFSLE LGSGQFIPGF
EEQLVGSKAG QTVDVNVTFP EDYQAEDLAG KDAKFVTTIH EVKTKEVPAL
DDELAKDIDD EVETLDELKA KYRKELESAK EIAFDDAVEG AAIELAVANA
EIVELPEEMV HDEVHRAMNE FMGNMQRQGI SPEMYFQLTG TTEEDLHKQY
QADADKRVKT NLVIEAIAAA EGFEATDEEI EKEITDLASE YNMEADQVRG
LLSADMLKHD IAMKKAVDVI TSSATVK

Seq. Id. No. 2

MSIITDVYAR EVLDSRGNPT LEVEVYTESG AFGRGMVPSG ASTGEHEAVE
LRDGDKSRYG GLGTQKAVDN VNNVIAEAII GYDVRDQQAI DRAMIALDGT
PNKGKLGANA ILGVSIAVAR AAADYLEVPL YSYLGGFNTK VLPTPMMNII
NGGSHSDAPI AFQEFMIMPV GAPTFKEALR WGAEVFHALK KILKERGLET
AVGDEGGFAP KFEGTEDGVE TILKAIEAAG YEAGENGIMI GFDCASSEFY
DAERKVYDYG KFEGEGGAVR TAAEQIDYLE ELVNKYPIIT IEDGMDENDW
DGWKALTERL GGRVQLVGDD FFVTNTDYLA RGIKEEAANS ILIKVNQIGT
LTETFEAIEM AKEAGYTAVV SHRSGETEDS TIADIAVATN AGQIKTGSLS
RTDRIAKYNQ LLRIEDQLGE VAQYKGIKSF YNLKK

Seq. Id. No. 3

MAYKTIYPYT NEVLHEFDNI SDSDLEQSLD IAHALYKTWR KEDNVEERQN
QLHKVADLLR KDRDKYAEVM TKDMGKLFTE AQGEVDLCAD IADYYADNGQ
KFLKPVPLES PNGEAYYLKQ AVGVLLAVEP WNFPFYQIMR VFAPNFIVGN
TMLLKHASIC PASAQAFEDL VREAGAPEGA FKNIFASYDQ VSNLISDPRV
AGVCLTGSER GGASIAAEAG KNLKKSSMEL GGNDAFLILD DADFDLLSKT
IFFARLYNAG QVCTSSKRFI VMADKYDEFV NMVVETFKSA KWGDPMDSET
TLAPLSSAGA KDDVLKQIKL AVDHGAEVVF GNDTIDHPGN FVMPTVLTNI
TKANPIYNQE IFGPVASIYK VDTEEEAIAL ANDSSYGLGS TVFSSDPEHA
KKVAAQIETG MTFINSGWTS LPELPFGGIK NSGYGRELSQ LGFDAFVNEH
LVFTPNSD

Seq. Id. No. 4

MAKEKYDRSK PHVNIGTIGH VDHGKTTLTA AITTVLARRL PTSVNQPKDY
ASIDAAPEER ERGITINTAH VEYETEKRHY AHIDAPGHAD YVKNMITGAA
QMDGAILVVA STDGPMPQTR EHILLSRQVG VKHLIVFMNK VDLVDDEELL
ELVEMEIRDL LSEYDFPGDD LPVIQGSALK ALEGDEKYED IIMELMSTVD
EYIPEPERDT DKPLLLPVED VFSITGRGTV ASGRIDRGTV RVNDEVEIVG
IKEDIQKAVV TGVEMFRKQL DEGLAGDNVG VLLRGVQRDE IERGQVLAKP
GSINPHTRFK GEVYILSKEE GGRHTPFFNN YRPQFYFRTT DVTGSIELPA
GTEMVMPGDN VTIEVELIHP IAVEQGTTFS IREGGRTVGS GIVSEIEA

Fig. 1

DIAGNOSTIC TEST OF *STREPTOCOCCUS AGALACTIAE* INFECTIONS

This application is a National Stage Application of PCT/PL2014/050018, filed Mar. 28, 2014, which claims priority to Polish Patent Application No. P404498, filed Jun. 28, 2013.

The object of the invention is a diagnostic test which enables confirmation of *Streptococcus agalactiae* infections in pregnant women. It utilizes a specific reaction of immunoreactive proteins obtained from clinical isolates of *Streptococcus agalactiae* with antibodies present in the serum of patients.

*Streptococcus agalactiae* (Group B *Streptococcus*, GB S), classified as serogroup B of streptococci, can colonize the lower gastrointestinal tract, anus and vagina without causing any symptoms of infection. It was confirmed that GBS is present in the vagina or rectum in approximately 10-30% of pregnant women. The colonization may be transient, chronic or intermittent. However, the presence of group B streptococci in the vagina in pregnancy is a significant risk factor for the development of infections in newborns. Intrauterine infections may occur in the course of pregnancy either via ascending infection or due to aspiration of infected amniotic fluid by the fetus. They might induce stillbirth, neonatal pneumonia, or sepsis. Colonization of a newborn may also occur during delivery but in such cases there is often only asymptomatic colonization of the skin and mucous membranes rather than development of infection [1, 2, 3]. According to the Regulation of the Minister of Health of 23 Sep. 2010 concerning the standards of conduct and medical procedures while providing health care services which fall within the scope of perinatal care exercised over women during physiological pregnancy, physiological childbirth, puerperium and infant care, all pregnant women should be screened for the presence of beta-hemolytic streptococci in the period between 33 and 37 weeks of gestation in swabs collected from the vulval vestibule and the anal area [4]. Confirmation of the presence of GBS is an indication for the implementation of perinatal antibiotic prophylaxis in the affected woman in accordance with the recommendations of the Polish Gynecological Society from 2008 [5]. Additionally, the pregnant women who developed a urinary tract infection with GBS or the bacteriological examination of their urine showed a positive result of culture for *Streptococcus agalactiae*, with a number equal to at least $1 \times 10^4$ (cfu/ml, i.e. colony forming units) (the so-called asymptomatic bacteriuria) should be given perinatal antibiotic prophylaxis because these women usually display a massive vaginal colonization with GBS, which significantly increases the risk of the development of early neonatal sepsis [1, 2, 5]. The proposed solution, however, is not fully effective, as it does not limit the development of infections in preterm neonates and does not protect from the development of late infections developing between 7 days and 3 months of age. Furthermore, more and more frequently, the problem of infections of GBS etiology affects other groups of patients, especially immunocompromised or geriatric patients [1, 2, 6].

Fast diagnosis of infections caused by GBS would ensure immediate implementation of antibiotic therapy but currently, on the market, there is no diagnostic test enabling confirmation of infection caused by *Streptococcus agalactiae*.

So far, the traditionally employed methods of diagnosis of *Streptococcus agalactiae* have mainly been based on the method of cultivation followed by phenotypic (biochemical), serological or molecular characteristics of the isolated and cultured microorganisms. The results obtained from these methods are available after several hours at the earliest, in the case of PCR, or after several days when it comes to conventional methods of cultivation [1, 2, 5].

The developed invention concerns a new diagnostic test allowing the confirmation of GBS infections in pregnant women, which utilizes a specific reaction of highly immunoreactive proteins obtained from *Streptococcus agalactiae* isolates with antibodies present in the serum of patients. The innovative test is characterized by a relatively short assay time, high sensitivity and specificity. This test is an alternative to the currently used solutions, such as bacteriological examination for group B streptococci carriage, based on the method of cultivation, which constitutes the so-called "gold standard" that is characterized by low sensitivity and a long time (up to several days) that one has to wait for the result and molecular biology techniques, including the method of real-time PCR, which allows to obtain the result quickly although it is very expensive and requires specialized equipment.

All pregnant women are the target group for our test. The developed method is suitable for application in all analytical and/or microbiological laboratories as it does not require the use of any special equipment. It is possible to extend the application of this assay to detect infections of GBS etiology in other groups of patients (e.g., neonates, outpatients, hospital patients) and in other clinical materials (e.g., plasma, cerebrospinal fluid).

An example of a known test, document WO2009122388A1, is a test based on the analysis of the nucleic acid of *Streptococcus agalactiae* strains isolated from blood, throat, mammary glands, nose, or vagina of women. In the present test, the marker sequence is a GBS gene called ssrA.

Another, similar, solution is described by document US20040009574A1. The solution concerns the identification of a nucleotide sequence encoding proteins responsible for the synthesis of capsular polysaccharides that are specific for *Streptococcus agalactiae* strains.

Document U.S. Pat. No. 8,137,673B2 is directed at the protein and its nucleotide sequence as a potential vaccine carrier and a diagnostic marker for groups A and B of *Streptococcus* strains. Fibronectin binding protein I is the marker protein.

Other potential marker proteins in *Streptococcus agalactiae* infections may be different polypeptides described in documents U.S. Pat. No. 7,262,024B2 and US20120141521A1.

The object of the invention is a protein comprising an amino acid sequence selected from: Seq. No. 1, Seq. No. 2, Seq. No. 3, Seq. No. 4 and the epitopes contained within them. It has been favorably isolated from a *Streptococcus agalactiae* strain, especially coming from a sample of blood, urine, vaginal smears, anus, ear, mouth, bronchial contents or cerebrospinal fluid obtained from a patient infected with this pathogen.

A further object of the invention is the use of the protein according to the invention defined above, to detect an infection with *Streptococcus agalactiae* strains.

The next object of the invention is a method for detecting patient infection with *Streptococcus agalactiae* strains, which is characterized by the fact that a sample taken from the patient is checked for the presence of the protein according to the invention defined above or of antibodies specific for said protein. The presence of said protein or of such antibodies indicates infection with *Streptococcus agalactiae* strains of patient. Preferably, the test is carried out using known immunochemical methods, especially Western Blotting or ELISA. Preferably, human serum is used as the test sample, especially in a dilution of 500-10,000 times.

In the research on the identification of immunoreactive proteins belonging to *Streptococcus agalactiae* strains, causing infections in humans, the obtained result was not obvious, namely, proteins of amino acid sequences marked with identification numbers of NRID1, NRID2, NRID3 and NRID4 (FIG. 1) were highly immunoreactive only with sera from individuals who underwent GBS infection and carriers of *Streptococcus agalactiae* bacteria. No similar reactivity was observed for sera of non-carriers of these bacterial strains.

The revealed method is a solution for rapid, sensitive and specific diagnosis of infection caused by *Streptococcus agalactiae*. The innovative approach in the developed test is the use of four highly immunoreactive amino acid sequences (NRID1, NRID2, NRID3, NRID4) belonging to proteins of *Streptococcus agalactiae* strains, which are the proteins on which the induction of natural antibodies occurs during the process of infection and sequences of which may serve as markers for identification of these infections in humans. The use of NRID1, NRID2, NRID3 and NRID4 sequences according to the invention is not only limited to the diagnostic test itself, but also, due to their immunogenic properties, they can be used as carriers for vaccines against GBS infections. Epitopes of NRID1, NRID2, NRID3 and NRID4 sequences may be further used to generate highly specific monoclonal antibodies and to develop an even faster and equally precise diagnostic test.

The method according to the invention comprises immunochemical methods such as Western Blotting, but is not only restricted to this method and may include other techniques, such as enzyme-linked immunosorbent assay (ELISA).

To explain the essence of the invention better, the description has been supplemented with the attached figures and the examples presented below.

FIG. 1 shows the amino acid sequences of immunoreactive *Streptococcus agalactiae* proteins.

Figure 2:
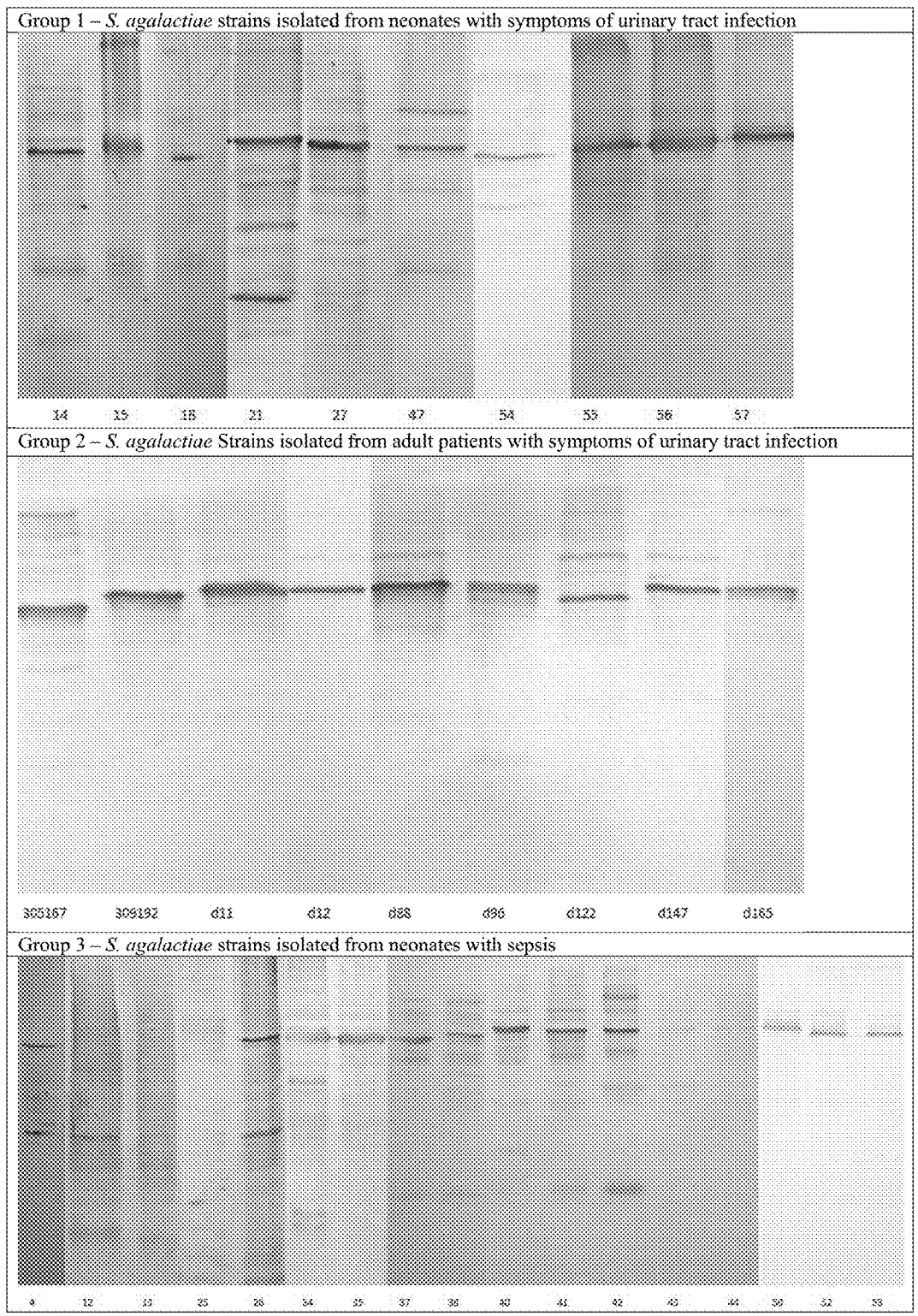
FIG. 2 shows the results of an immunoassay of a reaction of antibodies of human serum obtained from a pregnant woman infected with GBS (SB8) with proteins of *Streptococcus agalactiae* strains, taking into account the division into the studied groups.

EXAMPLE 1. THE IDENTIFICATION OF HIGHLY IMMUNOREACTIVE AMINO ACID SEQUENCES BELONGING TO PROTEINS OF *STREPTOCOCCUS AGALACTIAE* STRAINS

Clinical strains of *Streptococcus agalactiae* were divided into four groups (Table 1):

Group 1—strains isolated from the urine of neonates with symptoms of urinary tract infection (14, 15, 18, 21, 27, 47, 54, 55, 56, 57)

Group 2—strains isolated from the urine of adult patients with symptoms of urinary tract infection (305167, 309192, d11, d12, d88, d96, d122, d147, d165)

Group 3—strains isolated from blood, ear or mouth of neonates with sepsis (4, 12, 13, 25, 26, 34, 35, 37, 38, 40, 41, 42, 43, 44, 50, 52, 53)

Group 4—strains from carriage from neonates and pregnant women with no symptoms of infection with GBS and other strains of GBS (1, 2, 3, 5, 6, 7, 8, 9, 10, 11, 16, 17, 19, 20, 22, 23, 24, 28, 29, 30, 31, 32, 33, 36, 39, 45, 46, 48, 49, 51, 58, 59, 60)

TABLE 1

Characteristics of clinical isolates of *Streptococcus agalactiae* divided into test groups (Group 1, Group 2, Group 3) and a control group (Group 4).

| GBS isolate number | Serotype | The Alp family genes | Resistance phenotype | ST type | Clinical material | Clinical symptoms |
|---|---|---|---|---|---|---|
| Group 1 - *S. agalactiae* strains isolated from neonates with symptoms of urinary tract infection | | | | | | |
| 14 | /5279/08 | Ia | epsilon | — | — | Newborn's urine | Bacteriuria ($\geq 10^5$ cfu/ml) |
| 15 | /5303/08 | Ia | epsilon | — | — | Newborn's urine | Bacteriuria ($\geq 10^5$ cfu/ml) |
| 18 | /13695/08 | Ia | epsilon | — | — | Newborn's urine | Bacteriuria ($\geq 10^5$ cfu/ml) |
| 21 | /13608/08 | Ib | bca | — | — | Newborn's urine | Bacteriuria ($\geq 10^5$ cfu/ml) |
| 27 | /9353/08 | II | rib | — | — | Newborn's urine | Bacteriuria ($\geq 10^5$ cfu/ml) |
| 47 | /306723 | III | alp2 | — | ST-23 | Newborn's urine | Bacteriuria ($\geq 10^5$ cfu/ml) |
| 54 | /1716/08 | V | alp2 | — | — | Newborn's urine | Bacteriuria ($\geq 10^5$ cfu/ml) |
| 55 | /1736/08 | V | alp2 | cMLS$_B$ | — | Newborn's urine | Bacteriuria ($\geq 10^5$ cfu/ml) |
| 56 | /2992/08 | V | rib | — | — | Newborn's urine | Bacteriuria ($\geq 10^5$ cfu/ml) |
| 57 | /13793/08 | V | alp3 | cMLS$_B$ | — | Newborn's urine | Bacteriuria ($\geq 10^5$ cfu/ml) |
| Group 2 - *S. agalactiae* Strains isolated from adult patients with symptoms of urinary tract infection | | | | | | |
| 289370 | | II | rib | — | — | Urine - adult patient | Bacteriuria ($\geq 10^5$ cfu/ml) |
| 305167 | | Ia | epsilon | — | — | Urine - adult patient | Bacteriuria ($\geq 10^5$ cfu/ml) |
| 309192 | | II | bca | — | — | Urine - adult patient | Bacteriuria ($\geq 10^5$ cfu/ml) |

TABLE 1-continued

Characteristics of clinical isolates of *Streptococcus agalactiae* divided into test groups (Group 1, Group 2, Group 3) and a control group (Group 4).

| GBS isolate number | | Sero-type | The Alp family genes | Resistance phenotype | ST type | Clinical material | Clinical symptoms |
|---|---|---|---|---|---|---|---|
| d11 | | V | alp2 | cMLS$_B$ | — | Urine - adult patient | Bacteriuria (≥10$^5$ cfu/ml) |
| d12 | | III | rib | — | — | Urine - adult patient | Bacteriuria (≥10$^5$ cfu/ml) |
| d88 | | V | alp2 | — | — | Urine - adult patient | Bacteriuria (≥10$^5$ cfu/ml) |
| d96 | | Ia | epsilon | — | — | Urine - adult patient | Bacteriuria (≥10$^5$ cfu/ml) |
| d122 | | Ib | bca | — | — | Urine - adult patient | Bacteriuria (≥10$^5$ cfu/ml) |
| d147 | | III | rib | cMLS$_B$ | — | Urine - adult patient | Bacteriuria (≥10$^5$ cfu/ml) |
| d165 | | III | alp2/3 | — | — | Urine - adult patient | Bacteriuria (≥10$^5$ cfu/ml) |
| Group 3 - *S. agalactiae* strains isolated from neonates with sepsis | | | | | | | |
| 4 | /305245 | II | bca | — | ST-106 | Neonatal venous blood | Newborn sepsis (EOD) |
| 12 | /306735 | Ia | epsilon | — | ST-23 | Neonatal venous blood | Newborn sepsis (EOD) |
| 13 | /CM 169 | Ia | bca | — | ST-220 | Neonatal venous blood | Newborn sepsis (EOD) |
| 25 | /CM 47 | II | rib | cMLS$_B$ ermB | ST-19 | Neonatal venous blood | Newborn sepsis (EOD)/death |
| 34 | /5886/09 | III | rib | — | ST-17 | Neonatal venous blood | Newborn sepsis (EOD) |
| 35 | /3634/08 | III | rib | — | ST-17 | Neonatal venous blood | Newborn sepsis (EOD) |
| 37 | /L1-181 | III | rib | — | ST-17 | Neonatal venous blood | Newborn sepsis (EOD) |
| 38 | /4504/08 | III | rib | — | ST-19 | Neonatal venous blood | Newborn sepsis (EOD) |
| 40 | /W2/18 | III | alp2 | — | ST-23 | Neonatal venous blood | Newborn sepsis (EOD) |
| 41 | /CM 173 | III | bca | cMLS$_B$ ermB | ST-22 | Newborn's mouth smear | Newborn sepsis (EOD)/death |
| 42 | /CM 176 | III | rib | — | ST-220 | Newborn's mouth smear | Newborn sepsis (EOD)/death |
| 43 | /CM 185 | III | rib | iMLS$_B$ | ST-410 | Newborn's ear smear | Newborn sepsis (EOD) |
| 44 | /CM 28 | III | rib | — | ST-286 | Neonatal venous blood | Newborn sepsis (EOD) |
| 50 | /S1/4 | V | alp3 | — | ST-1 | Neonatal venous blood | Newborn sepsis (EOD)/death |
| 52 | /3514/08 | V | rib | — | ST-220 | Neonatal venous blood | Newborn sepsis (EOD) |
| 53 | /14030/08 | V | rib | M phenotype | ST-638 | Neonatal venous blood | Newborn sepsis (EOD) |
| Group 4 - *S. agalactiae* strains from carriage from newborns and pregnant women without symptoms of infection and other GBS strains | | | | | | | |
| 1 | /7/P/2a | Ia | epsilon | — | — | Vaginal smear - pregnant woman | Carrier state in pregnancy |
| 3 | /28/0/3a | III | rib | — | — | Anal smear - pregnant woman | Carrier state in pregnancy |
| 5 | /3/P/2a | V | alp3 | cMLS$_B$ ermB | — | Vaginal smear - pregnant woman | Carrier state in pregnancy |
| 6 | /10/P/3a | II | rib | — | — | Vaginal smear - pregnant woman | Carrier state in pregnancy |
| 7 | /42/P/3a | V | alp2 | — | — | Vaginal smear - pregnant woman | Carrier state in pregnancy |
| 8 | /9/0/2a | Ib | bca | — | — | Anal smear - pregnant woman | Carrier state in pregnancy |
| 9 | /14/P/3a | V | alp3 | cMLS$_B$ ermB | — | Vaginal smear - pregnant woman | Carrier state in pregnancy |
| 10 | /23/P/3a | II | rib | M phenotype mefA/E | — | Vaginal smear - pregnant woman | Carrier state in pregnancy |
| 11 | /25/P/1a | Ia | epsilon | — | — | Vaginal smear - pregnant woman | Carrier state in pregnancy |
| 16 | /13445/07 | Ia | epsilon | — | — | Newborn's mouth smear | Colonization of neonate |
| 17 | /11277/08 | Ia | rib | — | — | Newborn's ear smear | Colonization of neonate |
| 19 | /2337/08 | Ia | epsilon | — | — | Newborn's mouth smear | Colonization of neonate |
| 20 | /5338/08 | Ia | — | — | — | Newborn's mouth smear | Colonization of neonate |
| 22 | /D121 | Ib | epsilon | — | — | Cervical smear | Inflammation |
| 23 | /2107/08 | Ib | bca | — | — | Newborn's mouth smear | Colonization of neonate |
| 24 | /CM 184 | Ib | bca | — | — | Vaginal smear - pregnant woman | Colonization of neonate |

TABLE 1-continued

Characteristics of clinical isolates of *Streptococcus agalactiae* divided into test groups (Group 1, Group 2, Group 3) and a control group (Group 4).

| GBS isolate number | Sero-type | The Alp family genes | Resistance phenotype | ST type | Clinical material | Clinical symptoms |
|---|---|---|---|---|---|---|
| 28 | /13640/07 II | bca | — | ST-10 | Bronchial contents of neonate | Pneumonia |
| 29 | /14041/07 II | rib | — | — | Newborn's mouth smear | Colonization of neonate |
| 30 | /14191/07 II | bca | — | — | Newborn's ear smear | Colonization of neonate |
| 31 | /2341/08 II | rib | — | — | Newborn's mouth smear | Colonization of neonate |
| 32 | /D120 II | epsilon | M phenotype mefA/E | — | Vaginal smear | Inflammation |
| 33 | /D126 II | epsilon | — | — | Vaginal smear | Inflammation |
| 36 | /13723/07 III | rib | — | ST-358 | Newborn's ear smear | Colonization of neonate |
| 39 | /D136 III | epsilon | — | — | Vaginal smear | Inflammation |
| 45 | /3A-012 III | rib | — | ST-447 | Vaginal smear - pregnant woman | Colonization of neonate |
| 46 | /CM49 III | rib | — | ST-148 | Vaginal smear - pregnant woman | Colonization of neonate |
| 48 | /CM 87 III | rib | — | ST-19 | Newborn's ear smear | Colonization of neonate |
| 49 | /CM 3 IV | epsilon | — | — | Vaginal smear - pregnant woman | Colonization of neonate |
| 51 | /D156 V | epsilon | — | — | Vaginal smear | Inflammation |
| 58 | /104112 III | alp2 | — | — | ATCC | Reference strain |
| 59 | /2134 II | rib | — | — | DSM | Reference strain |
| 60 | /10511 V | rib | — | — | ATCC | Reference strain |

*Streptococcus agalactiae* strains were cultured in BHI solid medium in aerobic conditions for 24 h at 37° C. Cell mass after centrifugation was suspended in PBS to a concentration of A600=1.0. After centrifugation the pellet was suspended in Tris buffer (60 mM, pH 6.8) containing 2% SDS. The samples were then sonicated for 5 minutes. The protein supernatant obtained after centrifugation was precipitated with 3 vol. 95% ethanol overnight at 4° C. Samples were centrifuged and the pellet was dissolved in water. The BCA assay method (called Bicinchoninic acid assay) [7] served to determine the concentration of the isolated proteins.

Polyacrylamide Gel Electrophoresis Under Denaturing Conditions in the Presence of SDS According to Laemmli [8]

Electrophoretic separation of proteins was carried out according to the method described by Laemmli (1970) [7] in 5% stacking gel and 12.5% separating gel, in electrode buffer pH 8.6. Samples (10 µg) prior to application on gel (maximum volume of 10 µl) denatured for 5 minutes in a boiling heated bath. Separation of proteins was carried out for approximately 80 minutes, initially at the amperage of 10 mA on each plate with dimensions of 83×73×0.75 mm, and 20 mA after entry into stacking gel. Electrophoresis was performed in Bio-Rad Mini PROTEAN® 3 Cell kit for electrophoresis. After electrophoresis, gels were stained for 30 minutes at 0.1% (w/v) COOMASSIE® Brilliant Blue R-250 in 40% (v/v) methanol and 10% (v/v) acetic acid.

Immunoblotting [9]

The gel after polyacrylamide gel electrophoresis under denaturing conditions in the presence of SDS was transferred to Tris/Gly buffer with 10% (v/v) methanol of pH 8.3 (transfer buffer) for 15 minutes. The membrane, IMMO-BILON-P® (PVDF by Millipore), was soaked for 15 seconds in 100% MeOH, 2 minutes in MILLI-Q® water and 2 minutes in transfer buffer. Transfer was conducted for 1 h at 100 V using the Bio-Rad kit. After the transfer the membrane was stained in Ponceau S and then the excess dye was destained in MILLI-Q® water. Immunoblotting was performed with bound proteins on a hydrophobic IMMO-BILON-P® membrane. Free sites on the membrane were blocked with 1% bovine serum albumin (BSA) in Tris/HCl pH 7.5 buffer containing 50 mM NaCl and 0.05% (v/v) TWEEN®-20 (TBS-T buffer) for 1 h at 37° C. Excess BSA was washed with TBS-T, 1× for 15 minutes and 2 times for 5 minutes. Subsequently the reaction was conducted with 24 human sera (including 16 sera coming from pregnant women with GBS carriage and patients with infection; 8 sera constituted control and came from pregnant women who were not carriers of GBS), diluted in the range of 500-10,000 times in TBS-T with 1% BSA for 2 h at 37° C. with shaking. Excess of unbound antibodies was washed with TBS-T. The next stage of the experiment was the reaction with enzyme-labeled antibodies—alkaline phosphatase—in TBS-T for 1 h at 37° C. supplemented with 5% (v/v) goat serum. Excess conjugate was washed off with TBS-T (1×15 minutes, 4 times for 5 minutes). The image was developed using substrates for alkaline phosphatase: NBT (nitrotetrazole), BCIP (5-bromo-4-chloro-3-indolyl phosphate) in TBS buffer with the addition of Mg 2+ ions, pH 9.5. After obtaining the image (after about 15-20 seconds) the reaction was terminated by transferring the membrane to MILLI-O® water.

Results

As a result of the conducted experiments the image of immunogenic proteins of *Streptococcus agalactiae* strains was obtained. Images of reactive proteins of the tested strains differed from one another, and closer examination revealed correlation between the clinical material and the type of clinical symptoms of which the particular strain was isolated, and the reactivity with sera. It has been found that all the strains isolated from the urine of neonates (14, 15, 18, 21, 27, 47, 54, 55, 56, 57) and from the urine of adult patients (305167, 309192, d11, d12, d88, d96, d122, d147, d165) produce proteins in the range of 35-50 kDa which react with all the investigated sera originating from women with GBS carriage and with infection, but they do not react with sera from the control group.

Below are the results of immunoassay of the reaction of human serum antibodies obtained from a pregnant woman infected with GBS (sample number SB8) with proteins of Streptococcus agalactiae strains including the division into the studied groups of the isolated (FIG. 2).

The proteins in the range of 35-50 kDa showed reactivity with antibodies in the sera of patients with Streptococcus agalactiae infections, but did not react with sera obtained from healthy subjects who were not GBS carriers. The selected proteins reacted distinctively and can be used in immunoassays, such as Immunoblotting, ELISA, dot-EIA, for detection of S. agalactiae infections.

Proteins described above were isolated and their amino acid sequences determined. Identified in such way, highly immunoreactive amino acid sequences belonging to proteins of Streptococcus agalactiae strains are shown in the attached sequence listing as Seq. No. 1, Seq. No. 2, Seq. No. 3 and Seq. No. 4.

EXAMPLE 2. DIAGNOSTIC TEST OF STREPTOCOCCUS AGALACTIAE INFECTIONS

An exemplary embodiment of the invention comprises the following steps:
a) The prepared 0.45 μm thick PVDF membranes containing separated immunoreactive sequences of proteins of Streptococcus agalactiae strains according to the invention (Seq. Id. No. 1 to 4) are soaked in methanol, washed and subjected to reaction of free sites blocking using a blocking agent, preferably 0.5-5.0% BSA in phosphate buffer. At the same time the membrane is obtained by performing transfer of the separated GBS protein sequences from polyacrylamide gel, most preferably 7.5-15%, it is dried and stored in the dark.
b) The prepared PVDF membrane is incubated with human serum diluted 500-10,000 times, incubated on rocker at 37° C. for 1 h, excess of antibodies is washed away with phosphate buffer and detergent, preferably TWEEN®-20 in a concentration of 0.01-0.5%.
c) Reaction of immunoreactive sequences is performed on PVDF membrane with conjugated anti-human IgG antibodies with alkaline phosphatase at a dilution of 500-10,000 times on rocker at 37° C. for 1 h, excess conjugate is washed away with phosphate buffer with TWEEN®-20.
d) Test visualization using substrates for alkaline phosphatase.

REFERENCES

1. Schrag S, et al. Prevention of perinatal group B streptococcal disease. Revised guidelines from CDC. MMWR 2002; 15: 1-22.
2. Verani J, et al. Prevention of Perinatal Group B Streptococcal Disease. Revised Guidelines from CDC, 2010. MMWR 2010; 59: 1-32.
3. Rodriguez-Granger J, et al. Prevention of group B streptococcal neonatal disease revisited. The DEVANI European project. Eur J Clin Microbiol Infect Dis 2012; 31: 2097-104.
4. Regulation of the Minister of Health of 23 Sep. 2010 Annex to Regulation—Standards of conduct and medical procedures while providing health care services which fall within the scope of perinatal care exercised over women during physiological pregnancy, physiological childbirth, puerperium and infant care. 2010; 1-27.
5. Kotarski J, et al. Recommendations of the Polish Gynecological Society concerning the detection of group B streptococci (GBS) carriage in pregnant women and the prevention of infections in newborns. Ginekol Pol 2008; 79: 221-3.
6. Edwards M S, Baker C J. Group B Streptococcal infections in elderly adults. Clin Infect Dis 2005; 41:839-847.
7. Smith P K, et al. Measurement of protein using bincichoninic acid. Anal. Biochem. 1985; 150: 76-85
8. Laemmli U. K. Cleavage of structural proteins during the assembly of the head of bacteriophage T4. Nature 1970; 227: 680-5.
9. Towbin., T. Staechelin., J. Gordon. Electrophoretic transfer of proteins from polyacrylamide gels to ultracellulose sheets: Procedure and some applications. Proc. Natl. Acad. Sci. USA 76, 1979; 4350-4354.

The invention claimed is:

1. A method of detecting *Streptococcus agalactiae* in a patient comprising:
    obtaining a sample from the patient and
    detecting whether the amino acid sequence set forth in SEQ ID NO: 4 is present in the sample.

2. The method according to claim 1, wherein the detecting is carried out using Western Blotting or ELISA.

3. The method according to claim 1, wherein the detecting is carried out by incubating the sample with a human serum diluted 500-10,000 times, wherein the human serum contains antibodies to the amino acid sequence.

4. The method according to claim 1, wherein any of the amino acid sequence of SEQ ID NO: 1, SEQ ID NO: 2, or SEQ ID NO: 3 is additionally detected.

* * * * *

UNITED STATES PATENT AND TRADEMARK OFFICE
CERTIFICATE OF CORRECTION

PATENT NO. : 10,048,263 B2
APPLICATION NO. : 14/900620
DATED : August 14, 2018
INVENTOR(S) : Brzychczy-Włoch et al.

Page 1 of 1

It is certified that error appears in the above-identified patent and that said Letters Patent is hereby corrected as shown below:

On the Title Page

In Item (71):
"Applicants: UNIWERSYTET JAGIELLOŃSKI, Kraków (PL); INSTYTUT IMMUNOLOGII I TERAPII DÓSWIADCZALNEJ IM. LUDWIKA HIRSZFELDA PAN, Wroclaw (PL)"
Should read:
--Applicants: UNIWERSYTET JAGIELLOŃSKI, Kraków (PL); INSTYTUT IMMUNOLOGII I TERAPII DOŚWIADCZALNEJ IM. LUDWIKA HIRSZFELDA PAN, Wrocław (PL)--

In Item (72):
"Inventors: Monika Brzychczy-Wloch, Kraków (PL); Sabina Górska, Jaroslaw (PL); Ewa Brzozowska, Brzeg Dolny (PL); Andrzej Gamian, Wroclaw (PL); Piotr Heczko, Kraków (PL)"
Should read:
--Inventors: Monika Brzychczy-Włoch, Kraków (PL); Sabina Górska, Jarosław (PL); Ewa Brzozowska, Brzeg Dolny (PL); Andrzej Gamian, Wrocław (PL); Piotr Heczko, Kraków (PL)--

In Item (73):
"Assignees: Uniwersytet Jagiellonski, Cracow (PL); Instytut Immunologii I Terapii Doswiadczainej Im. Ludwika Hirszfelds Pan, Wroclaw (PL)"
Should read:
--Assignees: Uniwersytet Jagielloński, Kraków (PL); Instytut Immunologii I Terapii Doświadczalnej Im. Ludwika Hirszfelda Pan, Wrocław (PL)--

Signed and Sealed this
Sixteenth Day of October, 2018

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 427
<212> TYPE: PRT
<213> ORGANISM: Streptococcus agalactiae

<400> SEQUENCE: 1

Met Ser Thr Ser Phe Glu Asn Lys Ala Thr Asn Arg Gly Ile Ile Thr
1               5                   10                  15

Phe Thr Ile Ser Gln Asp Glu Ile Lys Pro Ala Leu Asp Gln Ala Phe
            20                  25                  30

Asn Lys Val Lys Lys Asp Leu Asn Val Pro Gly Phe Arg Lys Gly His
        35                  40                  45

Met Pro Arg Thr Val Phe Asn Gln Lys Phe Gly Glu Glu Ala Leu Tyr
    50                  55                  60

Glu Asn Ala Leu Asn Leu Val Leu Pro Lys Ala Tyr Glu Ala Ala Val
65                  70                  75                  80
```

-continued

```
Ala Glu Leu Gly Leu Asp Val Val Ala Gln Pro Lys Ile Asp Val Val
                85                  90                  95

Ser Met Glu Lys Gly Gln Asp Trp Lys Leu Thr Ala Glu Val Val Thr
            100                 105                 110

Lys Pro Glu Val Lys Leu Gly Asp Tyr Lys Asp Leu Ser Val Glu Val
            115                 120                 125

Asp Ala Ser Lys Glu Val Ser Asp Glu Val Asp Ala Lys Val Glu
            130                 135                 140

Arg Glu Arg Asn Asn Leu Ala Glu Leu Thr Val Lys Asp Gly Ala
145                 150                 155                 160

Ala Gln Gly Asp Thr Val Val Ile Asp Phe Val Gly Ser Val Asp Gly
                165                 170                 175

Val Glu Phe Asp Gly Lys Gly Asp Asn Phe Ser Leu Glu Leu Gly
            180                 185                 190

Ser Gly Gln Phe Ile Pro Gly Phe Glu Glu Gln Leu Val Gly Ser Lys
            195                 200                 205

Ala Gly Gln Thr Val Asp Val Asn Val Thr Phe Pro Glu Asp Tyr Gln
            210                 215                 220

Ala Glu Asp Leu Ala Gly Lys Asp Ala Lys Phe Val Thr Thr Ile His
225                 230                 235                 240

Glu Val Lys Thr Lys Glu Val Pro Ala Leu Asp Asp Glu Leu Ala Lys
                245                 250                 255

Asp Ile Asp Asp Glu Val Glu Thr Leu Asp Glu Leu Lys Ala Lys Tyr
                260                 265                 270

Arg Lys Glu Leu Glu Ser Ala Lys Glu Ile Ala Phe Asp Ala Val
            275                 280                 285

Glu Gly Ala Ala Ile Glu Leu Ala Val Ala Asn Ala Glu Ile Val Glu
            290                 295                 300

Leu Pro Glu Glu Met Val His Asp Glu Val His Arg Ala Met Asn Glu
305                 310                 315                 320

Phe Met Gly Asn Met Gln Arg Gln Gly Ile Ser Pro Glu Met Tyr Phe
                325                 330                 335

Gln Leu Thr Gly Thr Thr Glu Glu Asp Leu His Lys Gln Tyr Gln Ala
                340                 345                 350

Asp Ala Asp Lys Arg Val Lys Thr Asn Leu Val Ile Glu Ala Ile Ala
                355                 360                 365

Ala Ala Glu Gly Phe Glu Ala Thr Asp Glu Glu Ile Glu Lys Glu Ile
            370                 375                 380

Thr Asp Leu Ala Ser Glu Tyr Asn Met Glu Ala Asp Gln Val Arg Gly
385                 390                 395                 400

Leu Leu Ser Ala Asp Met Leu Lys His Asp Ile Ala Met Lys Lys Ala
                405                 410                 415

Val Asp Val Ile Thr Ser Ser Ala Thr Val Lys
                420                 425

<210> SEQ ID NO 2
<211> LENGTH: 435
<212> TYPE: PRT
<213> ORGANISM: Streptococcus agalactiae

<400> SEQUENCE: 2

Met Ser Ile Ile Thr Asp Val Tyr Ala Arg Glu Val Leu Asp Ser Arg
1               5                   10                  15

Gly Asn Pro Thr Leu Glu Val Glu Val Tyr Thr Glu Ser Gly Ala Phe
            20                  25                  30
```

```
Gly Arg Gly Met Val Pro Ser Gly Ala Ser Thr Gly Glu His Glu Ala
        35                  40                  45

Val Glu Leu Arg Asp Gly Asp Lys Ser Arg Tyr Gly Gly Leu Gly Thr
 50                  55                  60

Gln Lys Ala Val Asp Asn Val Asn Asn Val Ile Ala Glu Ala Ile Ile
 65                  70                  75                  80

Gly Tyr Asp Val Arg Asp Gln Gln Ala Ile Asp Arg Ala Met Ile Ala
                 85                  90                  95

Leu Asp Gly Thr Pro Asn Lys Gly Lys Leu Gly Ala Asn Ala Ile Leu
                100                 105                 110

Gly Val Ser Ile Ala Val Ala Arg Ala Ala Ala Asp Tyr Leu Glu Val
                115                 120                 125

Pro Leu Tyr Ser Tyr Leu Gly Gly Phe Asn Thr Lys Val Leu Pro Thr
        130                 135                 140

Pro Met Met Asn Ile Ile Asn Gly Gly Ser His Ser Asp Ala Pro Ile
145                 150                 155                 160

Ala Phe Gln Glu Phe Met Ile Met Pro Val Gly Ala Pro Thr Phe Lys
                165                 170                 175

Glu Ala Leu Arg Trp Gly Ala Glu Val Phe His Ala Leu Lys Lys Ile
        180                 185                 190

Leu Lys Glu Arg Gly Leu Glu Thr Ala Val Gly Asp Glu Gly Gly Phe
        195                 200                 205

Ala Pro Lys Phe Glu Gly Thr Glu Asp Gly Val Glu Thr Ile Leu Lys
210                 215                 220

Ala Ile Glu Ala Ala Gly Tyr Glu Ala Gly Glu Asn Gly Ile Met Ile
225                 230                 235                 240

Gly Phe Asp Cys Ala Ser Ser Glu Phe Tyr Asp Ala Glu Arg Lys Val
                245                 250                 255

Tyr Asp Tyr Gly Lys Phe Glu Gly Glu Gly Ala Val Arg Thr Ala
                260                 265                 270

Ala Glu Gln Ile Asp Tyr Leu Glu Glu Leu Val Asn Lys Tyr Pro Ile
        275                 280                 285

Ile Thr Ile Glu Asp Gly Met Asp Glu Asn Asp Trp Asp Gly Trp Lys
        290                 295                 300

Ala Leu Thr Glu Arg Leu Gly Gly Arg Val Gln Leu Val Gly Asp Asp
305                 310                 315                 320

Phe Phe Val Thr Asn Thr Asp Tyr Leu Ala Arg Gly Ile Lys Glu Glu
                325                 330                 335

Ala Ala Asn Ser Ile Leu Ile Lys Val Asn Gln Ile Gly Thr Leu Thr
                340                 345                 350

Glu Thr Phe Glu Ala Ile Glu Met Ala Lys Glu Ala Gly Tyr Thr Ala
        355                 360                 365

Val Val Ser His Arg Ser Gly Glu Thr Glu Asp Ser Thr Ile Ala Asp
        370                 375                 380

Ile Ala Val Ala Thr Asn Ala Gly Gln Ile Lys Thr Gly Ser Leu Ser
385                 390                 395                 400

Arg Thr Asp Arg Ile Ala Lys Tyr Asn Gln Leu Leu Arg Ile Glu Asp
                405                 410                 415

Gln Leu Gly Glu Val Ala Gln Tyr Lys Gly Ile Lys Ser Phe Tyr Asn
                420                 425                 430

Leu Lys Lys
        435
```

<210> SEQ ID NO 3
<211> LENGTH: 458
<212> TYPE: PRT
<213> ORGANISM: Streptococcus agalactiae

<400> SEQUENCE: 3

```
Met Ala Tyr Lys Thr Ile Tyr Pro Tyr Thr Asn Glu Val Leu His Glu
1               5                   10                  15

Phe Asp Asn Ile Ser Asp Ser Asp Leu Glu Gln Ser Leu Asp Ile Ala
            20                  25                  30

His Ala Leu Tyr Lys Thr Trp Arg Lys Glu Asp Asn Val Glu Glu Arg
        35                  40                  45

Gln Asn Gln Leu His Lys Val Ala Asp Leu Leu Arg Lys Asp Arg Asp
    50                  55                  60

Lys Tyr Ala Glu Val Met Thr Lys Asp Met Gly Lys Leu Phe Thr Glu
65                  70                  75                  80

Ala Gln Gly Glu Val Asp Leu Cys Ala Asp Ile Ala Asp Tyr Tyr Ala
                85                  90                  95

Asp Asn Gly Gln Lys Phe Leu Lys Pro Val Pro Leu Glu Ser Pro Asn
            100                 105                 110

Gly Glu Ala Tyr Tyr Leu Lys Gln Ala Val Gly Val Leu Leu Ala Val
        115                 120                 125

Glu Pro Trp Asn Phe Pro Phe Tyr Gln Ile Met Arg Val Phe Ala Pro
    130                 135                 140

Asn Phe Ile Val Gly Asn Thr Met Leu Leu Lys His Ala Ser Ile Cys
145                 150                 155                 160

Pro Ala Ser Ala Gln Ala Phe Glu Asp Leu Val Arg Glu Ala Gly Ala
                165                 170                 175

Pro Glu Gly Ala Phe Lys Asn Ile Phe Ala Ser Tyr Asp Gln Val Ser
            180                 185                 190

Asn Leu Ile Ser Asp Pro Arg Val Ala Gly Val Cys Leu Thr Gly Ser
        195                 200                 205

Glu Arg Gly Gly Ala Ser Ile Ala Ala Glu Ala Gly Lys Asn Leu Lys
    210                 215                 220

Lys Ser Ser Met Glu Leu Gly Gly Asn Asp Ala Phe Leu Ile Leu Asp
225                 230                 235                 240

Asp Ala Asp Phe Asp Leu Leu Ser Lys Thr Ile Phe Phe Ala Arg Leu
                245                 250                 255

Tyr Asn Ala Gly Gln Val Cys Thr Ser Ser Lys Arg Phe Ile Val Met
            260                 265                 270

Ala Asp Lys Tyr Asp Glu Phe Val Asn Met Val Val Glu Thr Phe Lys
        275                 280                 285

Ser Ala Lys Trp Gly Asp Pro Met Asp Ser Glu Thr Thr Leu Ala Pro
    290                 295                 300

Leu Ser Ser Ala Gly Ala Lys Asp Asp Val Leu Lys Gln Ile Lys Leu
305                 310                 315                 320

Ala Val Asp His Gly Ala Glu Val Val Phe Gly Asn Asp Thr Ile Asp
                325                 330                 335

His Pro Gly Asn Phe Val Met Pro Thr Val Leu Thr Asn Ile Thr Lys
            340                 345                 350

Ala Asn Pro Ile Tyr Asn Gln Glu Ile Phe Gly Pro Val Ala Ser Ile
        355                 360                 365

Tyr Lys Val Asp Thr Glu Glu Ala Ile Ala Leu Ala Asn Asp Ser
    370                 375                 380
```

```
Ser Tyr Gly Leu Gly Ser Thr Val Phe Ser Ser Asp Pro Glu His Ala
385                 390                 395                 400

Lys Lys Val Ala Ala Gln Ile Glu Thr Gly Met Thr Phe Ile Asn Ser
                405                 410                 415

Gly Trp Thr Ser Leu Pro Glu Leu Pro Phe Gly Gly Ile Lys Asn Ser
            420                 425                 430

Gly Tyr Gly Arg Glu Leu Ser Gln Leu Gly Phe Asp Ala Phe Val Asn
        435                 440                 445

Glu His Leu Val Phe Thr Pro Asn Ser Asp
    450                 455
```

<210> SEQ ID NO 4
<211> LENGTH: 398
<212> TYPE: PRT
<213> ORGANISM: Streptococcus agalactiae

<400> SEQUENCE: 4

```
Met Ala Lys Glu Lys Tyr Asp Arg Ser Lys Pro His Val Asn Ile Gly
1               5                   10                  15

Thr Ile Gly His Val Asp His Gly Lys Thr Thr Leu Thr Ala Ala Ile
            20                  25                  30

Thr Thr Val Leu Ala Arg Arg Leu Pro Thr Ser Val Asn Gln Pro Lys
        35                  40                  45

Asp Tyr Ala Ser Ile Asp Ala Ala Pro Glu Glu Arg Glu Arg Gly Ile
    50                  55                  60

Thr Ile Asn Thr Ala His Val Glu Tyr Glu Thr Glu Lys Arg His Tyr
65                  70                  75                  80

Ala His Ile Asp Ala Pro Gly His Ala Asp Tyr Val Lys Asn Met Ile
                85                  90                  95

Thr Gly Ala Ala Gln Met Asp Gly Ala Ile Leu Val Val Ala Ser Thr
            100                 105                 110

Asp Gly Pro Met Pro Gln Thr Arg Glu His Ile Leu Leu Ser Arg Gln
        115                 120                 125

Val Gly Val Lys His Leu Ile Val Phe Met Asn Lys Val Asp Leu Val
    130                 135                 140

Asp Asp Glu Glu Leu Leu Glu Leu Val Glu Met Glu Ile Arg Asp Leu
145                 150                 155                 160

Leu Ser Glu Tyr Asp Phe Pro Gly Asp Asp Leu Pro Val Ile Gln Gly
                165                 170                 175

Ser Ala Leu Lys Ala Leu Glu Gly Asp Glu Lys Tyr Glu Asp Ile Ile
            180                 185                 190

Met Glu Leu Met Ser Thr Val Asp Glu Tyr Ile Pro Glu Pro Glu Arg
        195                 200                 205

Asp Thr Asp Lys Pro Leu Leu Leu Pro Val Glu Asp Val Phe Ser Ile
    210                 215                 220

Thr Gly Arg Gly Thr Val Ala Ser Gly Arg Ile Asp Arg Gly Thr Val
225                 230                 235                 240

Arg Val Asn Asp Glu Val Glu Ile Val Gly Ile Lys Glu Asp Ile Gln
                245                 250                 255

Lys Ala Val Val Thr Gly Val Glu Met Phe Arg Lys Gln Leu Asp Glu
            260                 265                 270

Gly Leu Ala Gly Asp Asn Val Gly Val Leu Leu Arg Gly Val Gln Arg
        275                 280                 285

Asp Glu Ile Glu Arg Gly Gln Val Leu Ala Lys Pro Gly Ser Ile Asn
```

|     |     |     |     |     | 290 |     |     |     |     | 295 |     |     |     |     | 300 |
| --- | --- | --- | --- | --- | --- | --- | --- | --- | --- | --- | --- | --- | --- | --- | --- |
| Pro | His | Thr | Arg | Phe | Lys | Gly | Glu | Val | Tyr | Ile | Leu | Ser | Lys | Glu | Glu |
| 305 |     |     |     |     | 310 |     |     |     |     | 315 |     |     |     |     | 320 |
| Gly | Gly | Arg | His | Thr | Pro | Phe | Phe | Asn | Asn | Tyr | Arg | Pro | Gln | Phe | Tyr |
|     |     |     |     | 325 |     |     |     |     | 330 |     |     |     |     | 335 |     |
| Phe | Arg | Thr | Thr | Asp | Val | Thr | Gly | Ser | Ile | Glu | Leu | Pro | Ala | Gly | Thr |
|     |     |     | 340 |     |     |     |     | 345 |     |     |     |     | 350 |     |     |
| Glu | Met | Val | Met | Pro | Gly | Asp | Asn | Val | Thr | Ile | Glu | Val | Glu | Leu | Ile |
|     |     | 355 |     |     |     |     | 360 |     |     |     |     | 365 |     |     |     |
| His | Pro | Ile | Ala | Val | Glu | Gln | Gly | Thr | Thr | Phe | Ser | Ile | Arg | Glu | Gly |
|     | 370 |     |     |     |     | 375 |     |     |     |     | 380 |     |     |     |     |
| Gly | Arg | Thr | Val | Gly | Ser | Gly | Ile | Val | Ser | Glu | Ile | Glu | Ala |     |     |
| 385 |     |     |     |     | 390 |     |     |     |     | 395 |     |     |     |     |     |